United States Patent
Macielag et al.

(10) Patent No.: US 8,450,497 B2
(45) Date of Patent: May 28, 2013

(54) BENZIMIDAZOLE DERIVATIVES USEFUL AS TRPM8 CHANNEL MODULATORS

(75) Inventors: Mark J. Macielag, Spring House, PA (US); Mingde Xia, New Brunswick, NJ (US); Xiaoqing Xu, Plainsboro, NJ (US)

(73) Assignee: Janssen Pharmaceutica, NV (BE)

( * ) Notice: Subject to any disclaimer, the term of this patent is extended or adjusted under 35 U.S.C. 154(b) by 218 days.

(21) Appl. No.: 12/797,712

(22) Filed: Jun. 10, 2010

(65) Prior Publication Data

US 2011/0003800 A1 Jan. 6, 2011

Related U.S. Application Data

(60) Provisional application No. 61/185,681, filed on Jun. 10, 2009.

(51) Int. Cl.
*C07D 413/00* (2006.01)

(52) U.S. Cl.
USPC ........................................ 548/301.7; 548/126

(58) Field of Classification Search
None
See application file for complete search history.

(56) References Cited

FOREIGN PATENT DOCUMENTS

WO 2007/134107 A2 11/2007
WO 2009/012430 A1 1/2009

OTHER PUBLICATIONS

STN 7542824, Feb. 2, 1997.*
STN 5878633, Oct. 20, 1993.*
STN 5872511, Oct. 20, 1993.*
STN 1592171, Nov. 30, 1988.*
STN 823327, Nov. 28, 1988.*
McKemy, D.D., et al "Identification of a cold receptor reveals a general role for TRP channels in thermosensation", *Nature*, pp. 52-58, vol. 416 (6876), 2002.
Abe, J., et al. "Ca2+-dependent PKC activation mediates menthol-induced desensitization of transient receptor potential M8", *Neurosci Lett*, 2006, pp. 140-144, vol. 397(1-2).
Premkumar, L.S., et al. "Downregulation of Transient Receptor Potential Melastatin 8 by Protein Kinase C-Mediated Dephosphorylation", *J. Neurosci*, 2005, pp. 11322-11329, vol. 25(49).
Kobayashi, K., et al. "Distinct expression of TRPM8, TRPA1 and TRPV1 mRNAs in rat primary afferent neurons with a c-fibers and colocalization with Trk receptors" *J Comp Neurol*, 2005, pp. 596-606, vol. 493(4), 596-606.
Roza, C. et al., "Cold sensitivity in axotomized fibers of experimental neuromas in mice", *Pain*, 2006, pp. 24-36, vol. 120(1-2).
Xing, H., et al., "Chemical and Cold Sensitivity of Two Distinct populations of TRPM8-Expressing Somatosensory Neurons", *J Neurophysiol*, 2006, pp. 1221-1230, vol. 95(2).
Behrendt, H-J., et al., "Characterization of the mouse cold menthol receptor TRPM8 and vaniloid receptor type-1 VR1 using a fluormetric imaging plate reader (FLIPR) assay", *Brit J Pharmacol*, 2004, pp. 737-745, vol. 141(4).
Wei, E.T., et al., "AG-3-5: a chemical producing sensations of cold", *J Pharm Pharmacol.*, 1983, pp. 110-112, vol. 35.
International Search Report and Written Opinion, PCT/US2010/038135, dated Oct. 20, 2010, 12 pages.

\* cited by examiner

*Primary Examiner* — Shengjun Wang
*Assistant Examiner* — Svetlana M Ivanova

(57) ABSTRACT

Disclosed are compounds, compositions and methods for treating various diseases, syndromes, conditions and disorders, including pain. Such compounds are represented by Formula I as follows:

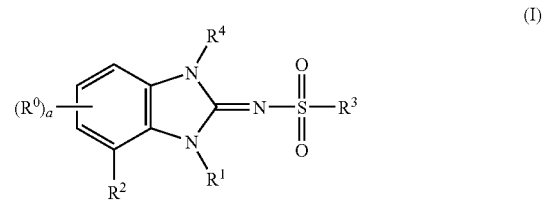

(I)

wherein $R^0$, $R^1$, $R^2$, $R^3$, $R^4$ and a are defined herein.

5 Claims, No Drawings

BENZIMIDAZOLE DERIVATIVES USEFUL AS TRPM8 CHANNEL MODULATORS

CROSS REFERENCE TO RELATED APPLICATIONS

This application claims the benefit of U.S. Provisional Application 61/185,681, filed on Jun. 10, 2009, which is incorporated by reference herein in its entirety.

STATEMENT REGARDING FEDERALLY SPONSORED RESEARCH OR DEVELOPMENT

The research and development of the invention described below was not federally sponsored.

FIELD OF THE INVENTION

The present invention is directed to benzimidazole derivatives, pharmaceutical compositions containing them and their use in the treatment of disorders and conditions modulated by the TRPM8 (transient receptor potential melastatin subfamily type 8) channel. The present invention also relates to processes for the preparation of benzimidazole derivatives and to their use in treating various diseases, syndromes, and disorders, including, those that cause inflammatory pain, neuropathic pain, cardiovascular diseases aggravated by cold, pulmonary diseases aggravated by cold, and combinations thereof.

BACKGROUND OF THE INVENTION

Transient receptor potential (TRP) channels are non-selective cation channels that are activated by a variety of stimuli. Numerous members of the ion channel family have been identified to date, including the cold-menthol receptor, also called TRPM8 (McKemy D. D., et al., *Nature* 2002, 416 (6876), 52-58). Collectively, the TRP channels and related TRP-like receptors connote sensory responsivity to the entire continuum of thermal stimulation, selectively responding to threshold temperatures ranging from noxious hot through noxious cold as well as to certain chemicals that mimic these sensations. Specifically, TRPM8 is known to be stimulated by cool to cold temperatures as well as by chemical agents such as menthol and icilin, which may be responsible for the therapeutic cooling sensation that these agents provoke.

TRPM8 is located on primary nociceptive neurons (A-δ and C-fibers) and is also modulated by inflammation-mediated second messenger signals (Abe, J., et al., *Neurosci Lett* 2006, 397(1-2), 140-144; Premkumar, L. S., et al., *J. Neurosci,* 2005, 25(49), 11322-11329). The localization of TRPM8 on both A-δ and C-fibers may provide a basis for abnormal cold sensitivity in pathologic conditions wherein these neurons are altered, resulting in pain, often of a burning nature (Kobayashi, K., et al., *J Comp Neurol,* 2005, 493(4), 596-606; Roza, C., et al., *Pain,* 2006, 120(1-2), 24-35; and Xing, H., et al., *J Neurophysiol,* 2006, 95(2), 1221-30). Cold intolerance and paradoxical burning sensations induced by chemical or thermal cooling closely parallel symptoms seen in a wide range of clinical disorders and thus provide a strong rationale for the development of TRPM8 modulators as novel antihyperalgesic or antiallodynic agents. TRPM8 is also known to be expressed in brain, lung, bladder, gastrointestinal tract, blood vessels, prostate and immune cells, thereby providing the possibility for therapeutic modulation in a wide range of maladies.

There is a need in the art for TRPM8 antagonists that can be used to treat a disease, syndrome, or condition in a mammal in which the disease, syndrome, or condition is affected by the modulation of TRPM8 channels, such as pain, the diseases that lead to such pain, and pulmonary or vascular dysfunction.

SUMMARY OF THE INVENTION

The present invention is directed to compounds of formula (I)

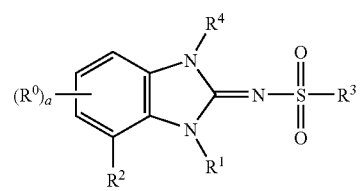

wherein
a is an integer from 0 to 3;
each $R^0$ is independently selected from the group consisting of halogen, hydroxy, cyano, lower alkyl, fluorinated lower alkyl, lower alkoxy and fluorinated lower alkoxy;
$R^2$ is selected from the group consisting of hydrogen, halogen, hydroxy, cyano, lower alkyl, fluorinated lower alkyl, lower alkoxy and fluorinated lower alkoxy;
$R^1$ is selected from the group consisting of alkyl, hydroxy substituted lower alkyl, halogenated lower alkyl, cycloalkyl-(lower alkyl)- and phenyl-(lower alkyl)-;
alternatively $R^2$ and $R^1$ are taken together as

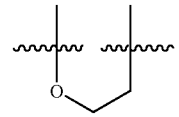 [SMILES: *CCO*]

(i.e. as —O—CH$_2$—CH$_2$—) or

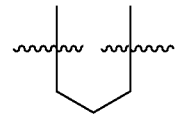

(i.e. as —CH$_2$—CH$_2$—CH$_2$—);
$R^3$ is selected from the group consisting of lower alkyl, cycloalkyl, aryl, heteroaryl, heterocycloalkyl, cycloalkyl-(lower alkyl)-, aryl-(lower alkyl)-, heteroaryl-(lower alkyl)- and heterocycloalkyl-(lower alkyl)-;
wherein the cycloalkyl, aryl, heteroaryl or heterocycloalkyl, whether alone or as part of a substituent group, is optionally substituted with one or more substituents independently selected from the group consisting of halogen, lower alkyl, halogenated lower alkyl, lower alkoxy, halogenated lower alkoxy, —C(O)OH, —C(O)O-(lower alkyl) and —C(O)—NR$^A$R$^B$;
wherein R$^A$ and R$^B$ are each independently selected from the group consisting of hydrogen and lower alkyl; alternatively R$^A$ and R$^B$ are taken together with the nitrogen atom to which they are bound to form a 5 to 6 membered, saturated nitrogen containing ring structure;

$R^4$ is selected from the group consisting of lower alkyl, cycloalkyl, aryl, heteroaryl, heterocycloalkyl, cycloalkyl-(lower alkyl)-, aryl-(lower alkyl)-, heteroaryl-(lower alkyl)- and heterocycloalkyl-(lower alkyl)-;

wherein the cycloalkyl, aryl, heteroaryl or heterocycloalkyl, whether alone or as part of a substituent group, is optionally substituted with one or more substituents independently selected from the group consisting of halogen, lower alkyl, halogenated lower alkyl, lower alkoxy, halogenated lower alkoxy and —S—$CF_3$;

provided that when $R^4$ is heteroaryl or heterocycloalkyl, then the $R^4$ group is bound to the N of the compound of formula (I) through a carbon atom;

provided that when a is 0, $R^1$ is methyl, $R^2$ is hydrogen and $R^4$ is methyl; then $R^3$ is other than methyl, phenyl or 4-methylphenyl;

and solvates, hydrates and pharmaceutically acceptable salts thereof.

The present invention is further directed to processes for the preparation of the compounds of formula (I). The present invention is further directed to a product prepared according to the process described herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder modulated by TRPM8 (selected from the group consisting of inflammatory pain (including visceral pain), neuropathic pain (including neuropathic cold allodynia), cardiovascular disease aggravated by cold and pulmonary disease aggravated by cold, in a subject in need thereof comprising administering to the subject a therapeutically effective amount of any of the compounds or pharmaceutical compositions described above.

Another example of the invention is the use of any of the compounds described herein in the preparation of a medicament wherein the medicament is prepared for treating: (a) inflammatory pain, (b) neuropathic pain, (c) cardiovascular disease aggravated by cold, or (d) pulmonary disease aggravated by cold, in a subject in need thereof.

DETAILED DESCRIPTION OF THE INVENTION

The present invention is directed to a process for the preparation of compound of formula (I)

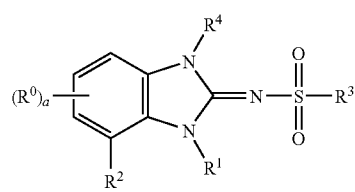

(I)

wherein a, $R^0$, $R^1$, $R^2$, $R^3$ and $R^4$ are as herein defined, and pharmaceutically acceptable salts thereof. The compounds of the present invention are useful in the treatment of disorders mediated by TRPM8, including inflammatory pain (including visceral pain), inflammatory hyperalgesia, neuropathic pain (including neuropathic cold allodynia), inflammatory somatic hyperalgesia, inflammatory visceral hyperalgesia, cardiovascular disease aggravated by cold and pulmonary disease aggravated by cold.

In an embodiment of the present invention, a is an integer from 0 to 2. In another embodiment of the present invention, a is an integer from 0 to 1. In another embodiment of the present invention, a is an integer form 1 to 2. In another embodiment of the present invention, a is 0.

In an embodiment of the present invention, each $R^0$ is selected from the group consisting of halogen, lower alkyl, fluorinated lower alkyl, lower alkoxy and fluorinated lower alkoxy. In another embodiment of the present invention, each $R^0$ is independently selected from the group consisting of halogen, $C_{1-2}$alkyl and fluorinated $C_{1-2}$alkyl. In another embodiment of the present invention, each $R^0$ is independently selected from the group consisting of fluoro, chloro, methyl and trifluoromethyl. In another embodiment of the present invention, each $R^0$ is independently selected from the group consisting of fluoro, chloro and trifluoromethyl. In another embodiment of the present invention, each $R^0$ is independently selected from the group consisting of chloro and trifluoromethyl.

In another embodiment of the present invention, each $R^0$ is independently selected from the group consisting of fluoro, chloro and methyl. In another embodiment of the present invention, each $R^0$ is independently selected from the group consisting of fluoro and methyl.

In an embodiment of the present invention, the $R^0$ group is bound at the 4-, 5- and/or 6-position of the benzimidazole core. In another embodiment of the present invention, the $R^0$ group is bound at the 5- and/or 6-position of the benzimidazole core.

In an embodiment of the present invention, $R^2$ is selected from the group consisting of hydrogen, halogen, lower alkyl, fluorinated lower alkyl, lower alkoxy and fluorinated lower alkoxy. In another embodiment of the present invention, $R^2$ is selected from the group consisting of hydrogen, halogen, lower alkyl and fluorinated lower alkyl. In another embodiment of the present invention, $R^2$ is hydrogen.

In an embodiment of the present invention, $R^1$ is selected from the group consisting of alkyl, hydroxy substituted lower alkyl, fluorinated lower alkyl, monocyclic cycloalkyl-(lower alkyl)- and phenyl-(lower alkyl)-. In another embodiment of the present invention, $R^1$ is selected from the group consisting of lower alkyl, fluorinated lower alkyl and monocyclic cycloalkyl-(lower alkyl)-. In an embodiment of the present invention, $R^1$ is selected from the group consisting of alkyl, hydroxy substituted lower alkyl, fluorinated lower alkyl, cycloalkyl-(lower alkyl)- and phenyl-(lower alkyl)-.

In another embodiment of the present invention, $R^1$ is selected from the group consisting of methyl, ethyl, isopropyl, isobutyl, 1-(2,2,2-trifluoroethyl) and cyclopropyl-methyl-, In another embodiment of the present invention, $R^1$ is selected from the group consisting of methyl, ethyl, isopropyl, 1-(2,2,2,-trifluoroethyl) and cyclopropyl-methyl-. In another embodiment of the present invention, $R^1$ is selected from the group consisting of methyl, ethyl, isopropyl and 1-(2,2,2-trifluoro-ethyl).

In another embodiment of the present invention, $R^1$ is selected from the group consisting of methyl, ethyl, isopropyl, isobutyl, 1-(2-hydroxy-ethyl), 1-(2,2,2-trifluoroethyl), benzyl and cyclopropyl-methyl-. In another embodiment of the present invention, $R^1$ is selected from the group consisting of methyl, ethyl and isopropyl. In another embodiment of the present invention, $R^1$ is selected from the group consisting of methyl and ethyl. In another embodiment of the present invention, $R^1$ is methyl.

In an embodiment of the present invention, alternatively $R^2$ and $R^1$ are taken together as

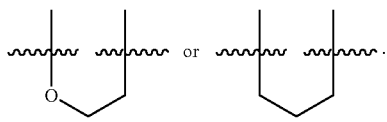 [SMILES: *CCO* ; *CCC*]

In another embodiment of the present invention, alternatively $R^2$ and $R^1$ are taken together as

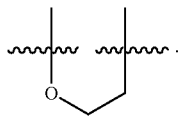 [SMILES: *CCO*]

In another embodiment of the present invention, alternatively $R^2$ and $R^1$ are taken together as

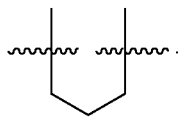

In an embodiment of the present invention, $R^3$ is selected from the group consisting of lower alkyl, monocyclic cycloalkyl, phenyl, monocyclic heteroaryl, monocyclic heterocycloalkyl, monocyclic cycloalkyl-(lower alkyl)-, phenyl-(lower alkyl)-, monocyclic heteroaryl-(lower alkyl)- and monocyclic heterocycloalkyl-(lower alkyl)-; wherein the monocyclic cycloalkyl, phenyl, monocyclic heteroaryl or monocyclic heterocycloalkyl, whether alone or as part of a substituent group, is optionally substituted with one to two substituents independently selected from the group consisting of halogen, lower alkyl, fluorinated lower alkyl, lower alkoxy, fluorinated lower alkoxy, —C(O)OH, —C(O)O-(lower alkyl) and —C(O)—$NR^A R^B$; wherein $R^A$ and $R^B$ are each independently selected from the group consisting of hydrogen and lower alkyl. In another embodiment of the present invention, $R^3$ is selected from the group consisting of lower alkyl, monocyclic cycloalkyl, phenyl, monocyclic cycloalkyl-(lower alkyl)- and phenyl-(lower alkyl)-; wherein the monocyclic cycloalkyl or phenyl, whether alone or as part of a substituent group, is optionally substituted with one or to two substituents independently selected from the group consisting of halogen, lower alkyl, fluorinated lower alkyl, lower alkoxy and fluorinated lower alkoxy. In another embodiment of the present invention, $R^3$ is phenyl; wherein the phenyl is optionally substituted with a substituent selected from the group consisting of halogen and fluorinated lower alkyl. In another embodiment of the present invention, $R^3$ is selected from the group consisting of phenyl, 4-fluorophenyl, 4-chlorophenyl and 4-trifluoromethylphenyl. In another embodiment of the present invention, $R^3$ is phenyl.

In another embodiment of the present invention, $R^3$ is selected from the group consisting of lower alkyl and phenyl; wherein the phenyl is optionally substituted with a substituent selected from the group consisting of halogen, lower alkyl and fluorinated lower alkyl. In another embodiment of the present invention, $R^3$ is selected from the group consisting of methyl, phenyl, 3-chlorophenyl, 4-chlorophenyl, 4-fluorophenyl, 4-methylphenyl and 4-trifluoromethylphenyl. In another embodiment of the present invention, $R^3$ is selected from the group consisting of methyl, phenyl, 4-fluorophenyl, 4-chlorophenyl and 4-methylphenyl. In another embodiment of the present invention, $R^3$ is selected from the group consisting of methyl, phenyl, 4-fluorophenyl and 4-chlorophenyl. In another embodiment of the present invention, $R^3$ is phenyl.

In an embodiment of the present invention, $R^4$ is selected from the group consisting of lower alkyl, monocyclic cycloalkyl, phenyl, monocyclic heteroaryl, monocyclic heterocycloalkyl, monocyclic cycloalkyl-(lower alkyl)-, phenyl-(lower alkyl)-, monocyclic heteroaryl-(lower alkyl)- and monocyclic heterocycloalkyl-(lower alkyl)-; wherein the monocyclic cycloalkyl, phenyl, monocyclic heteroaryl or monocyclic heterocycloalkyl, whether alone or as part of a substituent group, is optionally substituted with one to two substituents independently selected from the group consisting of halogen, lower alkyl, fluorinated lower alkyl, lower alkoxy, fluorinated lower alkoxy and —S—$CF_3$. In another embodiment of the present invention, $R^4$ is selected from the group consisting of lower alkyl, monocyclic cycloalkyl, phenyl, monocyclic cycloalkyl-(lower alkyl)- and phenyl-(lower alkyl)-; wherein the monocyclic cycloalkyl or phenyl, whether alone or as part of a substituent group, is optionally substituted with one to two substituents independently selected from the group consisting of halogen, lower alkyl, fluorinated lower alkyl, lower alkoxy, fluorinated lower alkoxy and —S—$CF_3$. In another embodiment of the present invention, $R^4$ is phenyl-(lower alkyl); wherein the phenyl portion of the phenyl-lower alkyl)-group is optionally substituted with one to two substituents independently selected from the group consisting of halogen, fluorinated lower alkyl, fluorinated lower alkoxy and —S—$CF_3$.

In another embodiment of the present invention, $R^4$ is selected from the group consisting of lower alkyl and phenyl-(lower alkyl); wherein the phenyl portion of the phenyl-(lower alkyl)-group is optionally substituted with one to two substituents independently selected from the group consisting of halogen, fluorinated lower alkyl, fluorinated lower alkoxy and —S—$CF_3$. In another embodiment of the present invention, $R^4$ is selected from the group consisting of benzyl, 4-fluoro-benzyl, 3,4-difluoro-benzyl, 3-chloro-4-fluoro-benzyl, 4-difluoromethyl-benzyl, 3-trifluoromethyl-benzyl, 4-trifluoromethyl-benzyl, 3-trifluoromethoxy-benzyl, 4-trifluoromethoxy-benzyl, 3-fluoro-4-trifluoromethyl-benzyl, 3-trifluoromethyl-4-fluoro-benzyl, 2-fluoro-5-trifluoromethyl-benzyl and 4-trifluoromethyl-thio-benzyl. In another embodiment of the present invention, $R^4$ is selected from the group consisting of 3-chloro-4-fluoro-benzyl, 3-trifluoromethyl-benzyl, 4-trifluoromethyl-benzyl, 3-trifluoromethoxy-benzyl, 4-trifluoromethoxy-benzyl, 3-fluoro-4-trifluoromethyl-benzyl and 2-fluoro-5-trifluoromethyl-benzyl. In another embodiment of the present invention, $R^4$ is selected from the group consisting of 4-trifluoromethyl-benzyl, 4-trifluoromethoxy-benzyl and 3-fluoro-4-trifluoromethyl-benzyl.

In another embodiment of the present invention, $R^4$ is selected from the group consisting of methyl, n-butyl, benzyl, 4-chlorophenyl, 4-fluoro-benzyl, 3,4-difluoro-benzyl, 3-chloro-4-fluoro-benzyl, 3-trifluoromethyl-benzyl, 4-trifluoromethoxy-benzyl, 3-trifluoromethoxy-benzyl, 4-trifluoromethoxy-benzyl, 3-trifluoromethyl-4-fluoro-benzyl, 3-fluoro-4-trifluoromethyl-benzyl, 2-fluoro-5-trifluoromethyl-benzyl, 4-difluoromethoxy-benzyl and 4-trifluoromethyl-thio-benzyl. In another embodiment of the present invention, $R^4$ is selected from the group consisting of n-butyl, benzyl, 4-fluoro-benzyl, 3,4-difluoro-benzyl, 3-trifluoromethyl-benzyl, 4-trifluoromethyl-benzyl, 4-difluoromethoxy-benzyl, 3-trifluoromethoxy-benzyl, 4-trifluoromethoxy-benzyl, 3-chloro-4-fluoro-benzyl, 3-trifluoromethyl-4-fluoro-benzyl, 3-fluoro-4-trifluoromethyl-benzyl, 2-fluoro-5-trifluoromethyl-benzyl and 4-trifluoromethyl-thio-benzyl. In another embodiment of the present invention, $R^4$ is selected from the group consisting of benzyl, 4-fluoro-benzyl, 3,4-difluoro-benzyl, 3-trifluoromethyl-benzyl, 4-trifluoromethyl-benzyl, 4-difluoromethoxy-benzyl, 3-trifluoromethoxy-benzyl, 4-trifluoromethoxy-benzyl, 3-chloro-4-fluoro-benzyl, 3-trifluoromethyl-4-fluoro-benzyl, 3-fluoro-4-trifluoromethyl-benzyl, 2-fluoro-5-trifluoromethyl-benzyl and 4-trifluoromethyl-thio-benzyl. In another embodiment of the present invention, $R^4$ is selected from the group consisting of 4-fluoro-benzyl, 3,4-difluoro-benzyl, 3-trifluoromethyl-benzyl, 4-trifluoromethyl-benzyl, 4-difluoromethoxy-benzyl, 3-trifluoromethoxy-benzyl, 4-trifluoromethoxy-benzyl, 3-chloro-4-fluoro-benzyl, 3-trifluoromethyl-4-fluoro-benzyl, 3-fluoro-4-trifluoromethyl-benzyl and 4-trifluoromethyl-thio-benzyl.

In an embodiment of the present invention, $R^4$ is other than methyl. In another embodiment of the present invention, $R^4$ is other than lower alkyl.

Additional embodiments of the present invention, include those wherein the substituents selected for one or more of the variables defined herein (i.e. a, $R^0$, $R^1$, $R^2$, $R^3$ and $R^4$) are independently selected to be any individual substituent or any subset of substituents selected from the complete list as defined herein. In another embodiment of the present invention is any single compound or subset of compounds selected from the representative compounds listed in Tables 1-2, below. Representative compounds of the present invention are as listed in Tables 1-2, below.

TABLE 1

Representative Compounds of Formula (I)

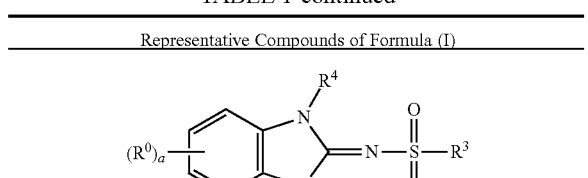

| ID No | $(R^0)_a$ | $R^1$ | $R^3$ | $R^4$ |
|---|---|---|---|---|
| 1 | a = 0 | methyl | phenyl | 3-trifluoromethyl-4-fluoro-benzyl |
| 2 | a = 0 | methyl | phenyl | 4-trifluoromethoxy-benzyl |
| 3 | a = 0 | methyl | phenyl | benzyl |
| 4 | a = 0 | methyl | phenyl | 3-trifluoromethyl-benzyl |
| 5 | a = 0 | methyl | phenyl | 3-trifluoromethoxy-benzyl |
| 6 | a = 0 | methyl | phenyl | 4-trifluoromethyl-benzyl |
| 7 | a = 0 | methyl | phenyl | 3,4-difluoro-benzyl |
| 8 | a = 0 | methyl | phenyl | 4-fluoro-benzyl |
| 9 | a = 0 | methyl | phenyl | 2-fluoro-5-trifluoromethyl-benzyl |
| 10 | a = 0 | methyl | phenyl | 3-fluoro-4-trifluoromethyl-benzyl |
| 11 | a = 0 | methyl | phenyl | 3-chloro-4-fluoro-benzyl |
| 12 | a = 0 | methyl | phenyl | 4-trifluoromethyl-thio-benzyl |
| 13 | a = 0 | methyl | phenyl | 4-difluoromethoxy-benzyl |
| 14 | a = 0 | ethyl | phenyl | 4-trifluoromethoxy-benzyl |
| 15 | a = 0 | ethyl | phenyl | 4-trifluoromethyl-benzyl |
| 16 | a = 0 | methyl | 4-fluoro-phenyl | 4-trifluoromethyl-benzyl |
| 17 | a = 0 | methyl | 4-fluoro-phenyl | 4-trifluoromethoxy-benzyl |
| 18 | a = 0 | methyl | 4-trifluoromethyl-phenyl | 4-trifluoromethoxy-benzyl |
| 19 | a = 0 | methyl | 4-chloro-phenyl | 4-trifluoromethyl-benzyl |
| 20 | a = 0 | methyl | 4-chloro-phenyl | 4-trifluoromethoxy-benzyl |
| 21 | a = 0 | methyl | 4-trifluoromethyl-phenyl | 4-trifluoromethyl-benzyl |
| 22 | a = 0 | methyl | 4-chloro-phenyl | 3-fluoro-4-trifluoromethyl-benzyl |
| 23 | a = 0 | methyl | 4-trifluoromethyl-phenyl | 3-fluoro-4-trifluoromethyl-benzyl |
| 24 | a = 0 | methyl | 4-fluoro-phenyl | 3-fluoro-4-trifluoromethyl-benzyl |
| 25 | a = 0 | ethyl | phenyl | 3-fluoro-4-trifluoromethyl-benzyl |
| 26 | a = 0 | isobutyl | phenyl | 3-fluoro-4-trifluoromethyl-benzyl |
| 27 | a = 0 | isobutyl | phenyl | 4-trifluoromethyl-benzyl |
| 28 | a = 0 | isobutyl | phenyl | 4-trifluoromethoxy-benzyl |
| 29 | 5-trifluoromethyl | methyl | phenyl | 4-trifluoromethyl-benzyl |
| 30 | 5-trifluoromethyl | methyl | phenyl | 4-trifluoromethoxy-benzyl |
| 31 | 5-trifluoromethyl | methyl | phenyl | 3-fluoro-4-trifluoromethyl-benzyl |
| 33 | 5-fluoro | ethyl | phenyl | 3-fluoro-4-trifluoromethyl-benzyl |
| 34 | 5-trifluoromethyl | isopropyl | phenyl | 4-trifluoromethoxy-benzyl |
| 35 | 5-trifluoromethyl | isopropyl | phenyl | 3-fluoro-4-trifluoromethyl-benzyl |
| 36 | 5-fluoro | ethyl | phenyl | 4-trifluoromethoxy-benzyl |
| 37 | 5-trifluoromethyl | ethyl | phenyl | 3-fluoro-4-trifluoromethyl-benzyl |
| 38 | 5-fluoro | methyl | phenyl | 4-trifluoromethyl-benzyl |
| 39 | 5-fluoro | ethyl | phenyl | 4-trifluoromethyl-benzyl |
| 40 | a = 0 | 1-(2,2,2-trifluoroethyl) | phenyl | 4-trifluoromethyl-benzyl |
| 41 | 5-fluoro | methyl | phenyl | 3-fluoro-4-trifluoromethyl-benzyl |
| 42 | 5-chloro | isopropyl | phenyl | 3-fluoro-4-trifluoromethyl-benzyl |
| 43 | a = 0 | 1-(2,2,2-trifluoro-ethyl) | phenyl | 3-fluoro-4-trifluoromethyl-benzyl |
| 44 | a = 0 | 1-(2,2,2-trifluoro-ethyl) | phenyl | 4-trifluoromethoxy-benzyl |
| 45 | 5-chloro | isopropyl | phenyl | 4-trifluoromethoxy-benzyl |
| 46 | 5-fluoro | methyl | phenyl | 4-trifluoromethoxy-benzyl |

TABLE 1-continued

Representative Compounds of Formula (I)

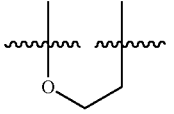 [SMILES: *CCO*]

| ID No | (R⁰)ₐ | R¹ | R³ | R⁴ |
|---|---|---|---|---|
| 48 | a = 0 | cyclopropyl-methyl- | phenyl | 4-trifluoromethoxy-benzyl |
| 49 | a = 0 | cyclopropyl-methyl- | phenyl | 4-trifluoromethyl-benzyl |
| 50 | a = 0 | cyclopropyl-methyl- | phenyl | 3-fluoro-4-trifluoromethyl-benzyl |
| 54 | 6-methyl | methyl | phenyl | 4-trifluoromethoxy-benzyl |
| 55 | 6-methyl | methyl | phenyl | 3-fluoro-4-trifluoromethyl-benzyl |
| 56 | 6-methyl | methyl | phenyl | 4-trifluoromethyl-benzyl |
| 57 | 6-trifluoro-methyl | methyl | phenyl | 3-fluoro-4-trifluoromethyl-benzyl |
| 58 | 6-trifluoro-methyl | methyl | phenyl | 4-trifluoromethoxy-benzyl |
| 59 | 6-trifluoro-methyl | methyl | phenyl | 4-trifluoromethyl-benzyl |
| 60 | 5,6-dimethyl | methyl | phenyl | 4-trifluoromethoxy-benzyl |
| 61 | 5,6-dimethyl | methyl | phenyl | 3-fluoro-4-trifluoromethyl-benzyl |
| 62 | 4-methyl | methyl | phenyl | 3-fluoro-4-trifluoromethyl-benzyl |

TABLE 2

Representative Compounds of Formula (I)

| ID No | —R² + R¹— | R³ | R² |
|---|---|---|---|
| 51 | (cyclopentyl bridge) | phenyl | 3-fluoro-4-trifluoromethyl-benzyl |
| 52 | (cyclopentyl bridge) | phenyl | 4-trifluoromethoxy-benzyl |
| 53 | (cyclopentyl bridge) | phenyl | 4-trifluoromethyl-benzyl |
| 63 | (tetrahydropyran bridge) | phenyl | 4-trifluoromethyl-benzyl |
| 64 | (tetrahydropyran bridge) | phenyl | 4-trifluoromethoxy-phenyl |

In another embodiment, the present invention is directed to a compound of formula (I) that exhibits a % Inhibition at 0.2 µM of greater than or equal to about 10% (preferably greater than or equal to about 25%, more preferably greater than or equal to about 80%, more preferably greater than or equal to about 80%), also preferred are greater than or equal to 20% at 0.5 uM, and further preferred are greater than or equal to 30% at 1 uM, as measured according to the procedure described in Biological Example 1, which follows herein. In an embodiment, the present invention is directed to a compound of formula (I) which exhibits an $IC_{50}$ of less than or 0.100 µM, preferably less than or equal to about 0.050 µM, more preferably less than or equal to about 0.025 µM, more preferably less than or equal to about 0.010 µM, more preferably less than or equal to about 0.005 µM, as measured according to the procedure described in Biological Example 1, which follows herein.

As used herein, unless otherwise noted, the term "halogen" refers to chlorine, bromine, fluorine and iodine.

As used herein, unless otherwise noted, the term "alkyl" whether used alone or as part of a substituent group, include straight and branched chains having 1 to 8 carbon atoms. Therefore, designated numbers of carbon atoms (e.g. $C_{1-8}$) refer independently to the number of carbon atoms in an alkyl moiety or to the alkyl portion of a larger alkyl-containing substituent. In substituent groups with multiple alkyl groups such as ($C_{1-6}$alkyl)₂amino- the $C_{1-6}$alkyl groups of the dialkylamino may be the same or different. For example, alkyl radicals include methyl, ethyl, propyl, isopropyl, butyl, isobutyl, sec-butyl, t-butyl, pentyl and the like. Unless otherwise noted, the term "lower" when used with alkyl means a carbon chain having 1-4 carbon atoms.

As used herein, unless otherwise noted, the term "halogenated lower alkyl" refers to any lower alkyl group as defined above substituted with at least one halogen atom, preferably substituted with a least one fluoro atom. Suitable examples include, but are not limited to, —$CF_3$, —$CH_2$—$CF_3$, —$CF_2$—$CF_2$—$CF_2$—$CF_3$, and the like. Similarly, unless otherwise noted, the term "fluorinated lower alkyl" refers to any lower alkyl group as defined above substituted with at least one fluoro atom. Suitable examples include but are not limited to —$CF_3$, —$CH_2$—$CF_3$, —$CF_2$—$CF_2$—$CF_2$—$CF_3$, and the like.

As used herein, unless otherwise noted, the term "hydroxy substituted alkyl" refers to an alkyl group as defined above substituted with at least one hydroxy group. Preferably, the alkyl group is substituted with one hydroxy group. Preferably, the hydroxy group is not bound at a carbon atom that is alpha to a nitrogen atom. More preferably, the alkyl group is substituted with a hydroxy group at the terminal carbon. Suitable examples include, but are not limited to, —CH₂—OH, —CH₂—CH₂—OH, —CH₂—CH(OH)—CH₃, and the like.

As used herein, unless otherwise noted, "alkoxy" refers to an oxygen ether radical of the above described straight or branched chain alkyl groups containing 1-8 carbon atoms. For example, methoxy, ethoxy, n-propoxy, sec-butoxy, t-butoxy, n-hexyloxy, n-octyloxy and the like.

As used herein, unless otherwise noted, the term "halogenated lower alkoxy" refers to any lower alkoxy group as defined above substituted with at least one halogen atom, preferably substituted with a least one fluoro atom. Suitable examples include, but are not limited to, —OCF₃, —OCH₂—CF₃, —OCF₂—CF₂—CF₂—CF₃, and the like. Similarly, unless otherwise noted, the term "fluorinated lower alkoxy" refers to any lower alkyl group as defined above substituted with at least one fluoro atom. Suitable examples include but are not limited to —OCF₃, —OCH₂—CF₃, —OCF₂—CF₂—CF₂—CF₃, and the like.

As used herein, unless otherwise noted, the term "aryl" refers to an unsaturated, aromatic monocyclic or bicyclic ring of 6 to 10 carbon members. Examples of aryl rings include phenyl and naphthyl.

As used herein, unless otherwise noted, the term "cycloalkyl" refers to saturated or partially saturated, monocyclic, polycyclic, or bridged hydrocarbon rings of 3 to 14 carbon atoms. Examples of such rings include cyclopropyl, cyclobutyl, cyclopentyl, cyclohexyl, cycloheptyl, 1,2,3,4-tetrahydronaphthyl, bicyclo[2.2.1]heptyl, bicyclo[2.2.2]octyl, and adamantyl.

As used herein, unless otherwise noted, "heteroaryl" refers to an aromatic monocyclic or bicyclic aromatic ring structure having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to three additional nitrogens. In the case of 6 membered rings, the heteroaryl ring preferably contains from one to three nitrogen atoms. For the case wherein the 6 membered ring has three nitrogens, at most two nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl and pyrazinyl. Unless otherwise noted, the heteroaryl is attached to its pendant group at any heteroatom or carbon atom that results in a stable structure.

As used herein, unless otherwise noted, the term "heterocycloalkyl" refers to any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heterocycloalkyl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, and the like.

When a particular group is "substituted" (e.g., alkyl, cycloalkyl, aryl, heteroaryl, heterocycloalkyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenylC₁-C₆alkylaminocarbonylC₁-C₆alkyl" substituent refers to a group of the formula

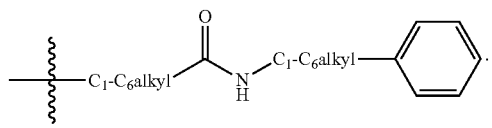

Unless otherwise noted, for compounds of formula (I), the R¹ group shall be denoted as bound to the 1-position, the R² group shall be denoted as bound at the 7-position, the R⁴ group shall be denoted as bound to the 3-position, and the R⁰ group(s) (which are bound to the benzo-fused portion of the benzimidazole core) shall be denoted as bound to the 3-, 4- and/or 5-positions according to the following numbering convention:

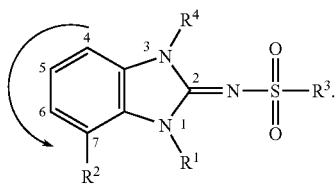

Abbreviations used in the specification, particularly the Schemes and Examples, are as follows:
DMF=N,N-Dimethylformamide
DMSO=Dimethylsulfoxide
EtOAc=Ethyl acetate
HPLC=High Performance Liquid Chromatography
MeOH=Methanol
MTBE=Methyl-t-butyl ether
Pd/C=Palladium on Carbon
TEA=Triethylamine
TFA=Trifluoroacetic Acid
THF=Tetrahydrofuran
TRPM8=Transient Receptor Potential M8 channel As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) delay or avoidance of the development of additional symptoms; and/or (d) delay or avoidance of the development of the disorder or condition.

One skilled in the art will recognize that wherein the present invention is directed to methods of prevention, a subject in need thereof (i.e., a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical professional to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

For the purposes of the present invention, the term "antagonist" is used to refer to a compound capable of producing, depending on the circumstance, a functional antagonism of an ion channel, including but not limited to competitive antagonists, non-competitive antagonists, desensitizing agonists, and partial agonists.

For purposes of the present invention, the term "TRPM8-modulated" is used to refer to the condition of being affected by the modulation of the TRPM8 channel, including but not limited to, the state of being mediated by the TRPM8 channel.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems. One skilled in the art will further recognize that wherein two consecutive reaction or process steps are run without isolation of the intermediate product (i.e. the product of the first of the two consecutive reaction or process steps), then the first and second reaction or process steps may be run in the same solvent or solvent system; or alternatively may be run in different solvents or solvent systems following solvent exchange, which may be completed according to known methods.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

Examples of suitable solvents, bases, reaction temperatures, and other reaction parameters and components are provided in the detailed descriptions which follows herein. One skilled in the art will recognize that the listing of said examples is not intended, and should not be construed, as limiting in any way the invention set forth in the claims which follow thereafter.

As used herein, unless otherwise noted, the term "aprotic solvent" shall mean any solvent that does not yield a proton. Suitable examples include, but are not limited to DMF, 1,4-dioxane, THF, acetonitrile, pyridine, dichloroethane, dichloromethane, MTBE, toluene, acetone, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, triflate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" refers to a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" refers to a group which may be attached to a oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles-Smoles)/(Rmoles+Smoles)]\times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([\alpha-obs]/[\alpha-max])\times 100.$$

One embodiment of the present invention is directed to a composition comprising the dextrorotatory enantiomer of a compound of formula (I) wherein said composition is substantially free from the levorotatory isomer of said compound. In the present context, substantially free means less than 25%, preferably less than 10%, more preferably less than 5%, even more preferably less than 2% and even more preferably less than 1% of the levorotatory isomer calculated as $$\% \text{ dextrorotatory} = \frac{(\text{mass dextrorotatory})}{(\text{mass dextrorotatory}) + (\text{mass levorotatory})} \times 100.$$

Another embodiment of the present invention is a composition comprising the levorotatory enantiomer of a compound of formula (I) wherein said composition is substantially free from the dextrorotatory isomer of said compound. In the present context, substantially free from means less than 25%, preferably less than 10%, more preferably less than 5%, even more preferably less than 2% and even more preferably less than 1% of the dextrorotatory isomer calculated as $$\% \text{ levorotatory} = \frac{(\text{mass levorotatory})}{(\text{mass dextrorotatory}) + (\text{mass levorotatory})} \times 100.$$

Embodiments of the present invention include prodrugs of compounds of formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid.

Representative bases that may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine and zinc hydroxide.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of formula (I) and at least one pharmaceutically acceptable carrier, pharmaceutically acceptable excipient, and/or pharmaceutically acceptable diluent.

By way of example, in the pharmaceutical compositions of embodiments of the present invention, the compounds of formula (I) may be admixed with any suitable binder(s), lubricant(s), suspending agent(s), coating agent(s), solubilizing agent(s), and combinations thereof.

Solid oral dosage forms, such as tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a white wax or white soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example intracavernosally, intravenously, intramuscularly, subcutaneously, intradermally or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations, such as suspensions, syrups, elixirs and solutions, suitable carriers, excipients and diluents include water, glycols, oils, alcohols, flavoring agents, preservatives, stabilizers, coloring agents and the like; for solid oral preparations, such as powders, capsules and tablets, suitable carriers, excipients and diluents include starches, sugars, diluents, granulating agents, lubricants, binders, disintegrating agents and the like. Solid oral preparations also may be optionally coated with substances, such as, sugars, or be enterically-coated so as to direct the major site of absorption and disintegration. For parenteral administration, the carrier, excipient and diluent will usually include sterile water; however other ingredients may be added to increase solubility and preservation of the composition. Injectable suspensions or solutions may also be prepared utilizing aqueous carriers along with appropriate additives, such as solubilizers and preservatives.

A therapeutically effective amount of a compound of formula (I) or a pharmaceutical composition thereof includes a dose range from about 0.1 mg to about 3000 mg, in particular from about 1 mg to about 1000 mg or, more particularly, from about 10 mg to about 500 mg of active ingredient in a regimen of about 1 to 4 times per day for an average (70 kg) human; although, it is apparent to one skilled in the art that the therapeutically effective amount for active compounds of the invention will vary as will the diseases, syndromes, conditions, and disorders being treated.

For oral administration, a pharmaceutical composition is preferably provided in the form of tablets containing about 1, about 10, about 50, about 100, about 150, about 200, about 250, and about 500 milligrams of the inventive compound as the active ingredient.

Advantageously, a compound of formula (I) may be administered in a single daily dose, or the total daily dosage may be administered in divided doses of two, three and four times daily.

Optimal dosages of a compound of formula (I) to be administered may be readily determined and will vary with the particular compound used, the mode of administration, the strength of the preparation, and the advancement of the disease, syndrome, condition, or disorder. In addition, factors associated with the particular subject being treated, including subject age, weight, diet and time of administration, will result in the need to adjust the dose to achieve an appropriate therapeutic level. The above dosages are thus exemplary of the average case. There can be, of course, individual instances wherein higher or lower dosage ranges are merited, and such are within the scope of this invention.

Compounds of formula (I) may be administered in any of the foregoing compositions and dosage regimens or by means of those compositions and dosage regimens established in the art whenever use of a compound of formula (I) is required for a subject in need thereof.

As antagonists of the TRPM8 channel, the compounds of formula (I) are useful in methods for treating and preventing a disease, a syndrome, a condition, or a disorder in a subject, including an animal, a mammal and a human in which the disease, the syndrome, the condition, or the disorder is affected by the modulation of TRPM8 channels. Such methods comprise, consist of, and consist essentially of administering to a subject, including an animal, a mammal, and a human in need of such treatment or prevention a therapeutically effective amount of a compound, salt, or solvate of formula (I). In particular, the compounds of formula (I) are useful for preventing or treating pain, or diseases, syndromes, conditions, or disorders causing such pain, or pulmonary or vascular dysfunction. More particularly, the compounds of formula (I) are useful for preventing or treating inflammatory pain, inflammatory hypersensitivity conditions, neuropathic pain, anxiety, depression, and cardiovascular disease aggravated by cold, including peripheral vascular disease, vascular hypertension, pulmonary hypertension, Raynaud's disease, and coronary artery disease, by administering to a subject in need thereof a therapeutically effective amount of a compound of formula (I).

Examples of inflammatory pain include pain due to a disease, condition, syndrome, disorder, or a pain state including inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, sinus headache, tension headache, or arachnoiditis.

One type of inflammatory pain is inflammatory hyperalgesia, which can be further distinguished as inflammatory somatic hyperalgesia or inflammatory visceral hyperalgesia. Inflammatory somatic hyperalgesia can be characterized by the presence of an inflammatory hyperalgesic state in which a hypersensitivity to thermal, mechanical and/or chemical stimuli exists. Inflammatory visceral hyperalgesia can also be characterized by the presence of an inflammatory hyperalgesic state, in which an enhanced visceral irritability exists.

Examples of inflammatory hyperalgesia include a disease, syndrome, condition, disorder, or pain state including inflammation, osteoarthritis, rheumatoid arthritis, back pain, joint pain, abdominal pain, musculoskeletal diseases, skin diseases, post operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity, itch, eczema, pharyngitis, enteritis, irritable bowel syndrome, inflammatory bowel diseases including Crohn's Disease or ulcerative colitis.

One embodiment of the present invention is directed to a method for treating inflammatory somatic hyperalgesia in which a hypersensitivity to thermal, mechanical and/or chemical stimuli exists, comprising the step of administering to a mammal in need of such treatment a therapeutically effective amount of a compound, salt or solvate of formula (I).

A further embodiment of the present invention is directed to a method for treating inflammatory visceral hyperalgesia in which an enhanced visceral irritability exists, comprising, consisting of, and/or consisting essentially of the step of administering to a subject in need of such treatment a therapeutically effective amount of a compound, salt or solvate of formula (I).

A further embodiment of the present invention is directed to a method for treating neuropathic cold allodynia in which a hypersensitivity to a cooling stimuli exists, comprising, consisting of, and/or consisting essentially of the step of administering to a subject in need of such treatment a therapeutically effective amount of a compound, salt or solvate of formula (I).

Examples of a neuropathic pain include pain due to a disease, syndrome, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, neuralgias (trigeminal neuralgia, glossopharyngeal neuralgia, postherpetic neuralgia and causalgia), lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vulvodynia, or vidian neuralgia.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, syndrome, disorder or pain state including neuropathic pain (neuralgia), pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

GENERAL SYNTHETIC METHODS

Compounds of formula (I) may be prepared according to the process outlined in Scheme 1.

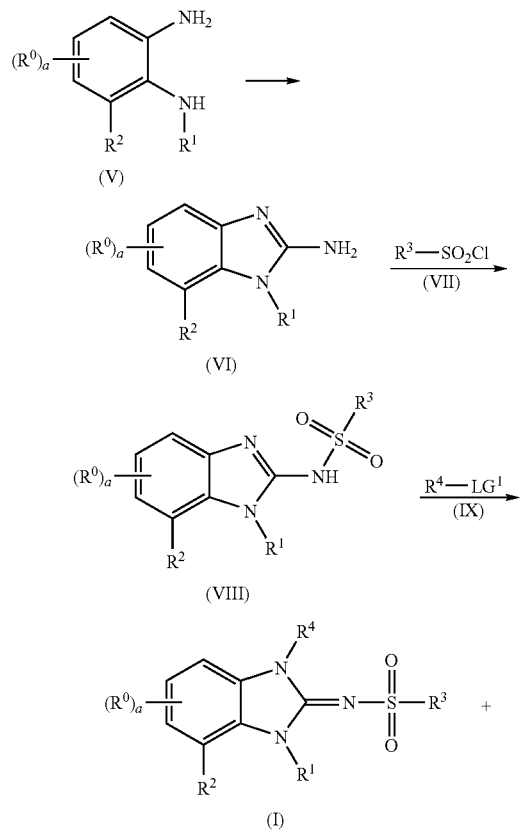

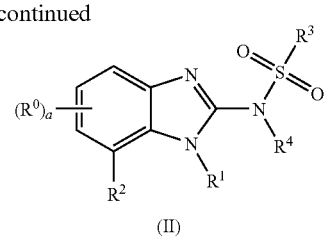

Accordingly, a suitably substituted compound of formula (V), a known compound or compound prepared by known methods, is reacted with cyanogen bromide, in an aqueous organic solvent such as methanol, ethanol, isopropanol, and the like, preferably at about room temperature, to yield the corresponding compound of formula (VI).

The compound of formula (VI) is reacted with a suitably substituted compound of formula (VII), a known compound or compound prepared by known methods, in the presence of an organic base such as pyridine, TEA, and the like, neat or in an organic solvent such as THF, methylene chloride, chloroform, and the like, preferably at about from room temperature to about 60° C., to yield the corresponding compound of formula (VIII).

The compound of formula (VIII) is reacted with a suitably substituted compound of formula (IX), wherein $LG^1$ is a suitably selected leaving group such as Br, Cl, and the like, in the presence of a base, preferably an inorganic base, such as $K_2CO_3$, $Na_2CO_3$, pyridine, TEA, and the like, in an organic solvent such as DMF, methylene chloride, acetonitrile, and the like, to yield a mixture of the corresponding compound of formula (I) and the corresponding compound of formula (II).

Preferably the compound of formula (I) is separated from the mixture, according to known methods, for example by column chromatography, HPLC, crystallization, and the like.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

N-[1-Methyl-3-(3-trifluoromethyl-benzyl)-1,3-dihydro-benzimidazol-2-ylidene]-benzenesulfonamide (Compound #4)

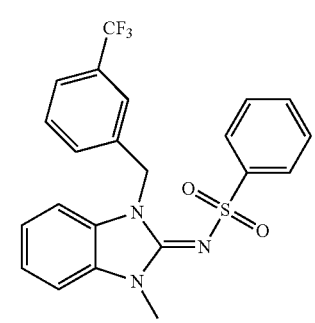 [SMILES: Cn1/c(=N/S(=O)(=O)c2ccccc2)n(Cc2cccc(C(F)(F)F)c2)c2ccccc21]

Step A: N-(1-Methyl-1H-benzimidazol-2-yl)-benzenesulfonamide

To a solution of 1-methyl-1H-benzimidazol-2-ylamine (2.65 g, 18.0 mmol) in anhydrous pyridine (15 mL) was added benzenesulfonyl chloride (2.30 mL, 18.0 mmol). The resulting mixture was stirred at 60° C. for 1 day. After addition of water, a precipitate was obtained, a mixture of N-(1-methyl-1H-benzimidazol-2-yl)-benzenesulfonamide and N-(1-benzenesulfonyl-3-methyl-1,3-dihydro-benzoimidazol-2-ylidene)-benzenesulfonamide. The mixture was then treated with 1 N NaOH. The insoluble part of the mixture was determined to be N-(1-benzenesulfonyl-3-methyl-1,3-dihydro-benzoimidazol-2-ylidene)-benzenesulfonamide. The alkaline solution was acidified with acetic acid and the resulting solid was collected by filtration, washed with $H_2O$, hexanes to yield N-(1-methyl-1H-benzimidazol-2-yl)-benzenesulfonamide. MS 288 $(M+1)^+$.

Step B: N-[1-Methyl-3-(3-trifluoromethyl-benzyl)-1,3-dihydro-benzimidazol-2-ylidene]-benzenesulfonamide To a solution of N-(1-methyl-1H-benzimidazol-2-yl)-benzenesulfonamide (100 mg, 0.35 mmol) in DMF (2 mL) was added 1-bromomethyl-3-trifluoromethyl-benzene (166.4 mg, 0.70 mmol) and potassium carbonate (48 mg). The resulting mixture was heated to 120° C. in a microwave reactor for 1 h and then diluted with EtOAc, washed with $H_2O$ and the organic layer was dried over $Na_2SO_4$, filtered, and concentrated in vacuo. The resultant residue was purified by flash column chromatography ($SiO_2$), eluting with a hexanes-EtOAc gradient to yield N-[1-methyl-3-(3-trifluoromethyl-benzyl)-1,3-dihydro-benzimidazol-2-ylidene]-benzenesulfonamide ($2^{nd}$ compound to elute off the column, 99.0 mg, 64%). MS 446 $(M+1)^+$.

The compounds of the present invention as listed in Table 3 below, were similarly prepared according to the procedure as described in Example 1 above, substituting suitably selected reagents, starting materials and purification methods known to those skilled in the art.

TABLE 3

| | Measured Mass Spec. |
|---|---|
| ID No. | MS $(M + 1)^+$ |
| 1 | 464 |
| 2 | 462 |
| 5 | 462 |
| 7 | 414 |
| 8 | 396 |
| 9 | 464 |
| 10 | 464 |
| 11 | 430 |
| 12 | 478 |
| 14 | 476 |
| 15 | 460 |
| 19 | 480 |
| 25 | 478 |
| 26 | 506 |
| 27 | 488 |
| 28 | 504 |

Example 2

N-[1-Ethyl-5-fluoro-3-(4-trifluoromethyl-benzyl)-1,3-dihydro-benzimidazol-2-ylidene]-benzenesulfonamide (Compound #39)

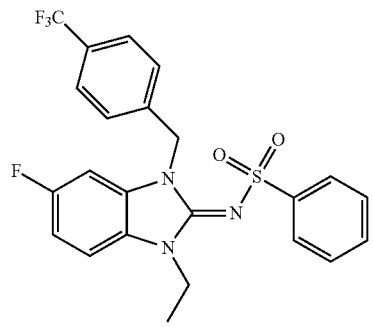 [SMILES: CCn1/c(=N/S(=O)(=O)c2ccccc2)n(Cc2ccc(C(F)(F)F)cc2)c2cc(F)ccc21]

Step A: 1-Ethyl-5-fluoro-1H-benzimidazol-2-ylamine

To a solution of $N^1$-ethyl-4-fluoro-benzene-1,2-diamine (1.54 g, 10.0 mmol) in MeOH (20 mL) and $H_2O$ (20 mL) was added cyanogen bromide (2.1 mL, 10.5 mmol, 5.0 M in acetonitrile). The resulting mixture was stirred at room temperature over night. The resulting mixture was then adjusted to pH>9 with concd $NH_4OH$ and the resulting solid was collected by filtration, washed with $H_2O$ and hexanes to yield 1-ethyl-5-fluoro-1H-benzimidazol-2-ylamine MS 180 $(M+1)^+$ Step B: N-(1-Ethyl-5-fluoro-1H-benzimidazol-2-yl)-benzenesulfonamide N-(1-Ethyl-5-fluoro-1H-benzoimidazol-2-yl)-benzenesulfonamide was prepared according to the procedure as described in Example 1, STEP A, substituting 1-ethyl-5-fluoro-1H-benzimidazol-2-ylamine for 1-methyl-1H-benzimidazol-2-ylamine. MS 320 $(M+1)^+$.

Step C: N-[1-Ethyl-5-fluoro-3-(4-trifluoromethyl-benzyl)-1,3-dihydro-benzimidazol-2-ylidene]-benzenesulfonamide N-[1-Ethyl-5-fluoro-3-(4-trifluoromethyl-benzyl)-1,3-dihydro-benzimidazol-2-ylidene]-benzenesulfonamide was prepared according to the procedure as described in Example 1, STEP B, substituting 1-bromomethyl-4-trifluoromethyl-benzene for 1-bromomethyl-3-trifluoromethyl-benzene, and further substituting N-(1-ethyl-5-fluoro-1H-benzimidazol-2-yl)-benzenesulfonamide for N-(1-methyl-1H-benzimidazol-2-yl)-benzenesulfonamide. MS 478 $(M+1)^+$.

The compounds of the present invention as listed in Table 4 below, were similarly prepared according to the procedure as described in Example 2 above, substituting suitably selected reagents, starting materials and purification methods known to those skilled in the art.

TABLE 4

| | Measured Mass Spec. |
|---|---|
| ID No. | MS (M + 1)+ |
| 29 | 514 |
| 30 | 530 |
| 31 | 532 |
| 33 | 496 |
| 34 | 558 |
| 35 | 560 |
| 36 | 494 |
| 37 | 546 |
| 42 | 526 |
| 45 | 524 |
| 51 | 490 |
| 52 | 488 |
| 53 | 472 |

Example 3

N-[1-(3-Fluoro-4-trifluoromethyl-benzyl)-3-(2,2,2-trifluoro-ethyl)-1,3-dihydro-benzimidazol-2-ylidene]-benzenesulfonamide (Compound #43)

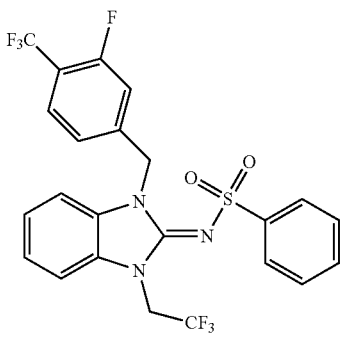 [SMILES: O=S(=O)(/N=c1\n(Cc2ccc(C(F)(F)F)c(F)c2)c2ccccc2n1CC(F)(F)F)c1ccccc1]

Step A: (2-Nitro-phenyl)-(2,2,2-trifluoro-ethyl)-amine

A mixture of 1-fluoro-2-nitro-benzene (1.55 g, 11.0 mmol), 2,2,2-trifluoro-ethylamine (3.27 g, 33.0 mmol) and DMSO (4.5 mL) was heated at 120° C. for 24 h. The resulting mixture was poured onto ice/H$_2$O and the resultant precipitate was collected by filtration, washed with H$_2$O and hexanes to yield (2-nitro-phenyl)-(2,2,2-trifluoro-ethyl)-amine MS 221 (M+1)+.

Step B: N-(2,2,2-Trifluoro-ethyl)-benzene-1,2-diamine

To a solution of (2-nitro-phenyl)-(2,2,2-trifluoro-ethyl)-amin (2.16 g, 9.8 mmol) in THF (6 mL) and MeOH (24 mL) at 0° C. was added ammonium formate (2.47 g, 39.2 mmol). The resulting mixture was purged with nitrogen, then 10% Pd/C (57 mg) was added. The ice bath was removed and the reaction mixture was stirred at room temperature for 5 h. The resulting mixture was filtered over CELITE®, washing with EtOAc. Removal of the solvent in vacuo yield N-(2,2,2-trifluoro-ethyl)-benzene-1,2-diamine, which was used in the next step without further purification. MS 191 (M+1)+.

Step C: 1-(2,2,2-Trifluoro-ethyl)-1H-benzimidazol-2-ylamine 1-(2,2,2-Trifluoro-ethyl)-1H-benzimidazol-2-ylamine was prepared according to the procedure as described in Example 2, STEP A above, substituting N-(2,2,2-trifluoro-ethyl)-benzene-1,2-diamine for N$^1$-ethyl-4-fluoro-benzene-1,2-diamine. MS 216 (M+1)+.

Step D: N-[1-(2,2,2-Trifluoro-ethyl)-1H-benzimidazol-2-yl]-benzenesulfonamide

N-[1-(2,2,2-Trifluoro-ethyl)-1H-benzimidazol-2-yl]-benzenesulfonamide was prepared according to the procedure as described in Example 1, STEP A, above, substituting 1-(2,2,2-trifluoro-ethyl)-1H-benzimidazol-2-ylamine for 1-methyl-1H-benzimidazol-2-ylamine MS 356 (M+1)+.

Step E: N-[1-(3-Fluoro-4-trifluoromethyl-benzyl)-3-(2,2,2-trifluoro-ethyl)-1,3-dihydro-benzimidazol-2-ylidene]-benzenesulfonamide N-[1-(3-Fluoro-4-trifluoromethyl-benzyl)-3-(2,2,2-trifluoro-ethyl)-1,3-dihydro-benzimidazol-2-ylidene]-benzenesulfonamide was prepared according to the procedure as described in Example 1, STEP B, above, substituting 4-bromomethyl-2-fluoro-1-trifluoromethyl-benzene for 1-bromomethyl-3-trifluoromethyl-benzene and further substituting N-[1-(2,2,2-trifluoro-ethyl)-1H-benzimidazol-2-yl]-benzenesulfonamide for N-(1-methyl-1H-benzimidazol-2-yl)-benzenesulfonamide. MS 532 (M+1)+.

Compound #44 (MS 530 (M+1)+) was similarly prepared according to the procedure as described above in Example 3, substituting suitably selected reagents, starting materials and purification methods known to those skilled in the art.

Example 4

N-[1-Cyclopropylmethyl-3-(3-fluoro-4-trifluoromethyl-benzyl)-1,3-dihydro-benzimidazol-2-ylidene]-benzenesulfonamide (Compound #50)

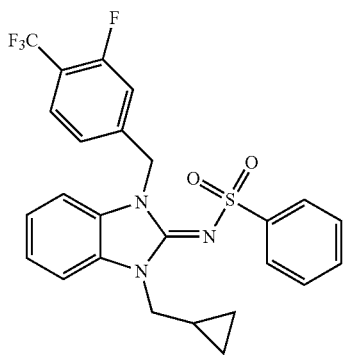 [SMILES: O=S(=O)(/N=c1\n(Cc2ccc(C(F)(F)F)c(F)c2)c2ccccc2n1CC1CC1)c1ccccc1]

Step A: N-Cyclopropylmethyl-benzene-1,2-diamine

To a solution of benzene-1,2-diamine (1.62 g, 15.0 mmol) and cyclopropanecarbaldehyde (1.05 g, 15.0 mmol) in MeOH (15 mL) at 0° C. was added NaCNBH$_3$ (2.07 g, 33.0 mmol) and acetic acid (0.2 mL). The ice bath was removed and the resulting mixture was stirred at room temperature over night.

The resulting mixture was diluted with EtOAc, washed with H₂O, dried over Na₂SO₄, filtered, and concentrated in vacuo. The resultant residue was purified by flash column chromatography (SiO₂), eluting with a hexanes-EtOAc gradient to yield N-cyclopropylmethyl-benzene-1,2-diamine (836 mg, 34%). MS 163 (M+1)⁺.

Step B: 1-Cyclopropylmethyl-1H-benzimidazol-2-ylamine

1-Cyclopropylmethyl-1H-benzimidazol-2-ylamine was prepared according to the procedure as described in Example 2, STEP A, substituting N-cyclopropylmethyl-benzene-1,2-diamine for N¹-ethyl-4-fluoro-benzene-1,2-diamine MS 188 (M+1)⁺.

Step C: N-(1-Cyclopropylmethyl-1H-benzimidazol-2-yl)-benzenesulfonamide

N-(1-Cyclopropylmethyl-1H-benzimidazol-2-yl)-benzenesulfonamide was prepared according to the procedure as described in Example 1, STEP A, substituting 1-cyclopropylmethyl-1H-benzimidazol-2-ylamine for 1-methyl-1H-benzimidazol-2-ylamine MS 328 (M+1)⁺.

Step D: N-[1-Cyclopropylmethyl-3-(3-fluoro-4-trifluoromethyl-benzyl)-1,3-dihydro-benzimidazol-2-ylidene]-benzenesulfonamide N-[1-Cyclopropylmethyl-3-(3-fluoro-4-trifluoromethyl-benzyl)-1,3-dihydro-benzimidazol-2-ylidene]-benzenesulfonamide was prepared according to the procedure as described in Example 1, STEP B, substituting 4-bromomethyl-2-fluoro-1-trifluoromethyl-benzene for 1-bromomethyl-3-trifluoromethyl-benzene and further substituting N-(1-cyclopropylmethyl-1H-benzimidazol-2-yl)-benzenesulfonamide for N-(1-methyl-1H-benzimidazol-2-yl)-benzenesulfonamide. MS 504 (M+1)⁺.

Compounds #48 (MS 502 (M+1)⁺) and #49 (MS 486 (M+1)⁺) were similarly prepared according to the procedure as described above in Example 4, substituting suitably selected reagents, starting materials and purification methods known to those skilled in the art.

Example 5

N-[1-(3-Fluoro-4-trifluoromethyl-benzyl)-3,5-dimethyl-1,3-dihydro-benzimidazol-2-ylidene]-benzene sulfonamide (Compound #55)

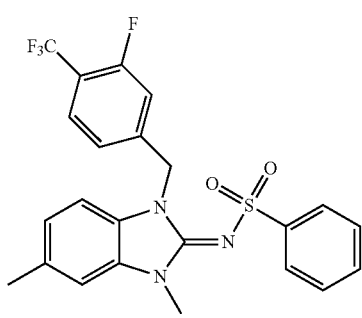 [SMILES: Cc1ccc2c(c1)n(C)/c(=N/S(=O)(=O)c1ccccc1)n2Cc1ccc(C(F)(F)F)c(F)c1]

Step A: Methyl-(5-methyl-2-nitro-phenyl)-amine

To a solution of 5-methyl-2-nitro-phenylamine (3.04 g, 20.0 mmol) in anhydrous DMF (20 mL) at 0° C. was portionwise added 95% NaH (528 mg, 22.0 mmol) and the resulting mixture stirred for 10 min. A solution of iodomethane (1.25 mL, 20.0 mmol) in anhydrous DMF (10 mL) was then added. The ice bath was removed and the resulting mixture was stirred at room temperature overnight. The resulting mixture was diluted with water, the solid was collected by filtration, washed with H₂O and hexanes to yield methyl-(5-methyl-2-nitro-phenyl)-amine MS 167 (M+1)⁺.

Step B: 4,N²-Dimethyl-benzene-1,2-diamine

To a solution of methyl-(5-methyl-2-nitro-phenyl)-amine (2.47 g, 14.9 mmol), ammonium formate (15 g, 237.9 mmol) in THF (7 mL) and MeOH (35 mL) at room temperature was added 10% Pd/C (650 mg) and the resulting mixture stirred at room temperature for 10 min. The resulting mixture was then filtered over CELITE® and concentrated in vacuo. The resulting residue was diluted with CH₂Cl₂, washed with H₂O and the organic layer was dried over Na₂SO₄, filtered, and concentrated in vacuo. The resultant residue was purified by flash column chromatography (SiO₂), eluting with a hexanes-EtOAc gradient to yield 4,N²-dimethyl-benzene-1,2-diamine.

Step C: 1,6-Dimethyl-1H-benzimidazol-2-ylamine 1,6-Dimethyl-1H-benzimidazol-2-ylamine was prepared according to the procedure as described in Example 2, STEP A, substituting 4,N²-dimethyl-benzene-1,2-diamine for N¹-ethyl-4-fluoro-benzene-1,2-diamine. MS 162 (M+1)⁺.

Step D: N-(1,6-Dimethyl-1H-benzimidazol-2-yl)-benzenesulfonamide

N-(1,6-Dimethyl-1H-benzimidazol-2-yl)-benzenesulfonamide was prepared according to the procedure as described in Example 1, STEP A, substituting 1,6-dimethyl-1H-benzimidazol-2-ylamine for 1-methyl-1H-benzimidazol-2-ylamine. MS 302 (M+1)⁺.

Step E: N-[1-(3-Fluoro-4-trifluoromethyl-benzyl)-3,5-dimethyl-1,3-dihydro-benzimidazol-2-ylidene]-benzenesulfonamide N-[1-(3-Fluoro-4-trifluoromethyl-benzyl)-3,5-dimethyl-1,3-dihydro-benzimidazol-2-ylidene]-benzenesulfonamide was prepared according to the procedure as described in Example 1, STEP B, substituting 4-bromomethyl-2-fluoro-1-trifluoromethyl-benzene for 1-bromomethyl-3-trifluoromethyl-benzene and further substituting N-(1,6-dimethyl-1H-benzimidazol-2-yl)-benzenesulfonamide for N-(1-methyl-1H-benzimidazol-2-yl)-benzenesulfonamide. MS 478 (M+1)⁺.

The compounds of the present invention as listed in Table 5 below, were similarly prepared according to the procedure as described in Example 5 above, substituting suitably selected reagents, starting materials and purification methods known to those skilled in the art.

TABLE 5

| ID No. | Measured Mass Spec. MS (M + 1)+ |
|---|---|
| 57 | 532 |
| 58 | 530 |
| 59 | 514 |
| 61 | 492 |
| 62 | 478 |

Example 6

N-[1-(4-Trifluoromethyl-benzyl)-3,4-dihydro-1H-5-oxa-1,2a-diaza-acenaphthylen-2-ylidene]-benzenesulfonamide TFA salt (Compound #63)

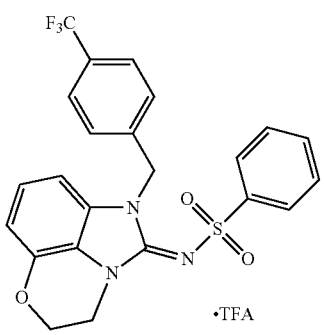 [SMILES: O=S(=O)(/N=c1\n(Cc2ccc(C(F)(F)F)cc2)c2cccc3c2n1CCO3)c1ccccc1]

Step A:
3,4-Dihydro-2H-benzo[1,4]oxazin-5-ylamine 3,4-Dihydro-2H-benzo[1,4]oxazin-5-ylamine was prepared according to the procedure as described in Example 5, STEP B, substituting 5-nitro-3,4-dihydro-2H-benzo[1,4]oxazine for 4,$N^2$-dimethyl-benzene-1,2-diamine MS 151 (M+1)+.

Step B: 3,4-Dihydro-5-oxa-1,2a-diaza-acenaphthylen-2-ylamine 3,4-Dihydro-5-oxa-1,2a-diaza-acenaphthylen-2-ylamine was prepared according to the procedure as described in Example 2, STEP A, substituting 3,4-dihydro-2H-benzo[1,4]oxazin-5-ylamine for $N^1$-ethyl-4-fluoro-benzene-1,2-diamine MS 176 (M+1)+.

Step C: N-(3,4-Dihydro-5-oxa-1,2a-diaza-acenaphthylen-2-yl)-benzenesulfonamide

N-(3,4-Dihydro-5-oxa-1,2a-diaza-acenaphthylen-2-yl)-benzenesulfonamide was prepared according to the procedure as described in Example 1, STEP A, substituting 3,4-dihydro-5-oxa-1,2a-diaza-acenaphthylen-2-ylamine for 1-methyl-1H-benzimidazol-2-ylamine MS 316 (M+1)+.

Step D: N-[1-(4-Trifluoromethyl-benzyl)-3,4-dihydro-1H-5-oxa-1,2a-diaza-acenaphthylen-2-ylidene]-benzenesulfonamide trifluoroacetic acid salt To a solution of N-(3,4-dihydro-5-oxa-1,2a-diaza-acenaphthylen-2-yl)-benzenesulfonamide (125 mg, 0.40 mmol) in DMF (2.5 mL) was added 1-bromomethyl-4-trifluoromethyl-benzene (190 mg, 0.80 mmol) and potassium carbonate (55 mg). The resulting mixture was heated to 120° C. in a microwave reactor for 1 h and then diluted with EtOAc, washed with $H_2O$ and the organic layer was dried over $Na_2SO_4$, filtered, and concentrated in vacuo. The resultant residue was purified by flash column chromatography ($SiO_2$), eluting with a hexanes-EtOAc gradient to yield N-[1-(4-trifluoromethyl-benzyl)-3,4-dihydro-1H-5-oxa-1,2a-diaza-acenaphthylen-2-ylidene]-benzenesulfonamide ($2^{nd}$ compound to elute off the column); which was further purified by HPLC (reverse phase C-18 column, 45-100% acetonitrile/water containing 0.05% trifluoroacetic acid) to yield N-[1-(4-trifluoromethyl-benzyl)-3,4-dihydro-1H-5-oxa-1,2a-diaza-acenaphthylen-2-ylidene]-benzenesulfonamide trifluoroacetic acid salt. MS 474 (M+1)+.

Compound #64 (MS 490 (M+1)+) was similarly prepared according to the procedure as described above in Example 6, substituting suitably selected reagents, starting materials and purification methods known to those skilled in the art.

Biological Example 1

In Vitro Canine TRPM8 Functional Assay

The functional activity of representative compounds of the formula (I) of the present invention was quantified by measuring changes in intracellular calcium concentration using a $Ca^{2+}$-sensitive fluorescent dye. The changes in fluorescent signal were monitored by a fluorescence plate reader, either a FLIPR™ (Molecular Devices) or FDSS (Hamamatsu). Increases in intracellular $Ca^{2+}$ concentration were readily detected upon activation with icilin.

HEK293 cells stably expressing canine TRPM8 were routinely grown as monolayers in Dulbecco's minimum essential medium supplemented with 10% FBS, 2 mM L-glutamine, 100 units/mL penicillin, 100 ug/mL streptomycin and 400 µg/mL G418. Cells were maintained in 5% $CO_2$ at 37° C. At 24 hr prior to assay, cells were seeded in black wall, clear-base poly-D-lysine coated 384-well plates (BD Biosciences, NJ, USA) at a density of 5,000 cells per well in culture medium and grown overnight in 5% $CO_2$ at 37° C. On assay day, growth media was removed, and cells were loaded with Calcium 3 Dye (Molecular Devices) for 35 min at 37° C., under 5% $CO_2$ and then incubated for 25 min at room temperature and atmosphere. Subsequently, cells were tested for agonist-induced increases in intracellular $Ca^{2+}$ levels using FLIPR™ or FDSS. Cells were treated with compounds of the formula (I) at varying concentrations and intracellular $Ca^{2+}$ was measured for 5 min prior to the addition of icilin to all wells to achieve a final concentration that produces approximately an 80% maximal response. $EC_{50}$ or $IC_{50}$ values for compounds of the present invention were determined from eight-point concentration-response studies and represent the concentration of compound required to elicit or inhibit 50% of the maximal response, respectively.

Maximal fluorescence intensity (FI) achieved upon addition of icilin was exported from the FLIPR or FDSS software and further analyzed using GraphPad Prism 3.02 (Graph Pad Software Inc., CA, U.S.A.). Basal FI was subtracted prior to normalizing data to percent of maximal response. Curves were generated using the average of quadruplicate wells for each data point using nonlinear regression of either sigmoidal dose response or sigmoidal dose response (variable slope).

Finally, the $EC_{50}$ and $IC_{50}$ values were calculated with the best-fit curve determined by GraphPad Prism Representative compounds of the present invention were tested according to the procedures as described in Biological Example 1 above, with results as listed in Table 6, below.

TABLE 6

Biological Activity Measurements

| ID No | $IC_{50}$ (µM) | % Inh @ 0.2 µM |
|---|---|---|
| 1 | | 40 |
| 2 | | 34 |
| 3 | | 8 |
| 4 | | 42 |
| 5 | | 50 |
| 6 | | 2 |
| 7 | | 24 |
| 8 | | 20 |
| 9 | | 39 |
| 10 | | 22 |
| 11 | | 38 |
| 12 | | 11 |
| 13 | | 9 |
| 14 | 0.100 | 75 |
| 15 | 0.069 | 85 |
| 16 | | 1 |
| 17 | | 6 |
| 18 | | 1 |
| 19 | | 13 |
| 20 | | 2 |
| 21 | | 8 |
| 22 | | 6 |
| 23 | | 3 |
| 24 | | 3 |
| 25 | | 62 |
| 26 | 0.014 | 100 |
| 27 | 0.043 | 71 |
| 28 | 0.058 | 70 |
| 29 | | 19 |
| 30 | | 17 |
| 31 | 0.039 | 71 |
| 33 | | 70 |
| 34 | 0.024 | 95 |
| 35 | 0.010 | 100 |
| 36 | | 36 |
| 37 | 0.005 | 93 |
| 38 | | 1 |
| 39 | | 26 |
| 40 | | 9 |
| 41 | | 6 |
| 42 | 0.026 | 95 |
| 43 | 0.021 | 89 |
| 44 | | 37 |
| 45 | | 66 |
| 46 | | 1 |
| 48 | | 67 |
| 49 | 0.110 | 71 |
| 50 | 0.086 | 94 |
| 51 | | 14 |
| 52 | | 18 |
| 53 | | 16 |
| 54 | | 6 |
| 55 | | 18 |
| 56 | | 1 |
| 57 | | 45 |
| 58 | | 25 |
| 59 | | 20 |
| 60 | | 5 |
| 61 | | 14 |
| 62 | | 19 |
| 63 | | 34 |
| 64 | | 61 |

Representative compounds of the present invention as listed in Table 7, below were re-tested according to the procedure as described above. Test samples were prepared by diluting a 10 mM stock solution of test compound with 100% DMSO prior to addition to assay buffer.

TABLE 7

Biological Activity Measurements

| ID No | $IC_{50}$ (µM) | % Inh @ 1µM |
|---|---|---|
| 3 | | 40 |
| 6 | | 65 |
| 13 | 0.764 | 55 |
| 16 | | 57 |
| 17 | 0.606 | 60 |
| 18 | 0.635 | 57 |
| 20 | 0.430 | 74 |
| 21 | 0.588 | 59 |
| 22 | 0.512 | 77 |
| 23 | 0.764 | 59 |
| 24 | 0.379 | 85 |
| 38 | | 24 |
| 40 | 0.426 | 57 |
| 41 | | 79 |
| 46 | | 58 |
| 54 | 0.645 | 55 |
| 56 | | 40 |
| 60 | | 48 |

Biological Example 2

Icilin was initially developed as a "super-cooling" compound by Delmar Chemicals Ltd. Subsequently it was shown to be one of the most potent known agonists of TRPM8 (McKemy D D, et al. Nature 2002, 416(6876): 52-8), having an $EC_{50}$=0.2 µM in stimulating calcium ion influx into TRPM8 transfected cells (Behrendt H J et al. Brit J Pharmacol 2004, 141(4): 737-45). Initial in vivo testing of icilin showed it to cause "wet-dog" shakes in rats. Similar shaking or jumping behavior was also evident in mice, rabbits, cats, dogs and monkeys. In humans, icilin produced a sensation of coolness on contact with mucous membranes, cold prickling when 0.1 mg was dropped on the tongue and coldness in the mouth, pharynx and chest lasting 30-60 minutes when 5-10 mg was ingested orally (Wei E T, Seid D A, J Pharm Pharmacol. 1983, 35, 110). The inhibition or reversal of icilin-induced shaking behaviors in rodents provides evidence for the utility of TRPM8 antagonists in treating or preventing a disease or condition in a mammal in which the disease or condition is affected by the modulation of TRPM8 receptors.

Inhibition of Icilin-Induced "Wet-Dog" Shakes in Rats

Male Sprague Dawley rats (22-450 g, Charles River Labs, n=6-9/treatment) were used to evaluate the ability of test compounds to block icilin-induced "wet-dog" shakes (WDS). The test compound was administered at 10 mg/kg in an appropriate vehicle, such as hydroxypropyl-β-cyclodextrin (HP-β-CD), methocellulose, 10% Solutol, $H_2O$ or the like, by the appropriate route (e.g., i.p or p.o), 30-60 min before icilin. Icilin was then administered in PEG-400 or 10% solutol/$H_2O$, at 1.0 or 3.0 mg/kg, i.p. and spontaneous "wet-dog" shakes were counted 10-20 min post-icilin.

A representative compound of the present invention was tested at 10 mg/kg p.o. and 60 min pre-icilin, according to the procedure described above. Results, as listed in Table 8 below, are presented as a percent inhibition of shakes, which was calculated as [1−(test compound WDS count/vehicle WDS count)]×100.

TABLE 8

| | Inhibition of icilin-induced "wet-dog" shakes in rats | |
|---|---|---|
| ID No. | Vehicle | % Inhibition |
| 37 | 0.5% HPMC | 0.6 |

Solid Dosage Formulation

As a specific embodiment of an oral composition, 100 mg of Compound #37, prepared as in Example 2, is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (I)

wherein:
a is an integer from 0 to 2;
each $R^0$ is independently selected from the group consisting of halogen, $C_{1-2}$alkyl, and fluorinated $C_{1-2}$alkyl;
$R^2$ is hydrogen;
$R^1$ is selected from the group consisting of lower alkyl, fluorinated lower alkyl and monocyclic cycloalkyl-(lower alkyl)-;
alternatively $R^2$ and $R^1$ are taken together as $R^3$ is phenyl; wherein the phenyl is optionally substituted with a substituent selected from the group consisting of halogen and fluorinated lower alkyl;
$R^4$ is selected from the group consisting of benzyl, 4-fluoro-benzyl, 3,4-difluoro-benzyl, 3-chloro-4-fluoro-benzyl, 4-difluoromethyl-benzyl, 3-trifluoromethyl-benzyl, 4-trifluoromethyl-benzyl, 3-trifluoromethoxy-benzyl, 4-trifluoromethoxy-benzyl, 3-fluoro-4-trifluoromethyl-benzyl, 3-trifluoromethyl-4-fluoro-benzyl, 2-fluoro-5-trifluoromethyl-benzyl and 4-trifluoromethyl-thio-benzyl;
provided that when a is 0, $R^1$ is methyl, $R^2$ is hydrogen and $R^4$ is methyl; then $R^3$ is other than methyl, phenyl, or 4-methylphenyl;
or pharmaceutically acceptable salt thereof.

2. A compound as in claim 1, wherein
a is an integer from 0 to 1;
$R^0$ is selected from the group consisting of fluoro, chloro, and trifluoromethyl;
$R^2$ is hydrogen;
$R^1$ is selected from the group consisting of methyl, ethyl, isopropyl, 1 (2,2,2,-trifluoroethyl), cyclopropyl-methyl-;
alternatively $R^2$ and $R^1$ are taken together as $R^3$ is phenyl;
$R^4$ is selected from the group consisting of 3-chloro-4-fluoro-benzyl, 3-trifluoromethyl-benzyl, 4-trifluoromethyl-benzyl, 3 trifluoromethoxy-benzyl, 4-trifluoromethoxy-benzyl, 3-fluoro-4-trifluoromethyl-benzyl and 2-fluoro-5-trifluoromethyl-benzyl;
or pharmaceutically acceptable salt thereof.

3. A compound as in claim 2, wherein
a is an integer from 0 to 1;
$R^0$ is selected from the group consisting of chloro and trifluoromethyl;
$R^2$ is hydrogen;
$R^1$ is selected from the group consisting of methyl, ethyl, isopropyl, 1-(2,2,2-trifluoro-ethyl) and cyclopropyl-methyl-;
$R^3$ is phenyl;
$R^4$ is selected from the group consisting of 4-trifluoromethyl-benzyl, 4-trifluoromethoxy-benzyl and 3-fluoro-4-trifluoromethyl-benzyl;
or pharmaceutically acceptable salt thereof.

4. A compound as in claim 3, wherein
a is an integer from 0 to 1;
$R^0$ is selected from the group consisting of chloro and trifluoromethyl;
$R^2$ is hydrogen;
$R^1$ is selected from the group consisting of methyl, ethyl, isopropyl and 1-(2,2,2-trifluoro-ethyl);
$R^3$ is phenyl;
$R^4$ is selected from the group consisting of 4-trifluoromethyl-benzyl, 4-trifluoromethoxy-benzyl and 3-fluoro-4-trifluoromethyl-benzyl;
or pharmaceutically acceptable salt thereof.

5. A pharmaceutical composition comprising a pharmaceutically acceptable carrier and a compound of claim 1.

* * * * *